(12) United States Patent
Shi et al.

(10) Patent No.: US 10,736,835 B2
(45) Date of Patent: Aug. 11, 2020

(54) SPRAYABLE GEL COMPOSITION FOR HAIR CONDITIONING

(71) Applicant: Henkel AG & Co. KGaA, Duesseldorf (DE)

(72) Inventors: Yi Shi, Shanghai (CN); Xiaowei Chang, Shanghai (CN)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/780,526

(22) PCT Filed: Dec. 9, 2015

(86) PCT No.: PCT/CN2015/096803
§ 371 (c)(1),
(2) Date: May 31, 2018

(87) PCT Pub. No.: WO2017/096554
PCT Pub. Date: Jun. 15, 2017

(65) Prior Publication Data
US 2018/0344620 A1 Dec. 6, 2018

(51) Int. Cl.
| | |
|---|---|
| *A61K 8/892* | (2006.01) |
| *A61Q 5/12* | (2006.01) |
| *A61K 8/34* | (2006.01) |
| *A61K 8/04* | (2006.01) |
| *A61K 8/891* | (2006.01) |
| *A61K 8/41* | (2006.01) |
| *A61K 8/81* | (2006.01) |
| *A61K 8/895* | (2006.01) |

(52) U.S. Cl.
CPC .............. *A61K 8/892* (2013.01); *A61K 8/042* (2013.01); *A61K 8/046* (2013.01); *A61K 8/34* (2013.01); *A61K 8/342* (2013.01); *A61K 8/41* (2013.01); *A61K 8/8152* (2013.01); *A61K 8/891* (2013.01); *A61K 8/895* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 5,340,570 A | 8/1994 | Wong et al. | |
| 2002/0061284 A1 | 5/2002 | Dupuis | |
| 2006/0110358 A1* | 5/2006 | Hsu ................... | A61K 31/4412 424/85.6 |
| 2007/0264204 A1 | 11/2007 | Noor et al. | |
| 2009/0098079 A1 | 4/2009 | Schiemann et al. | |
| 2013/0171080 A1 | 7/2013 | Sarkar et al. | |

FOREIGN PATENT DOCUMENTS

| | | | |
|---|---|---|---|
| WO | 199014404 A1 | 12/1992 | |
| WO | WO-2014146818 A1 * | 9/2014 | ........... A61K 8/0229 |

OTHER PUBLICATIONS

State Intellectual Property Office of the People's Republic of China International Search Report and Written Opinion issued in International Application No. PCT/CN2015/096803 dated Sep. 18, 2016.

* cited by examiner

*Primary Examiner* — David J Blanchard
*Assistant Examiner* — Sarah J Chickos
(74) *Attorney, Agent, or Firm* — Lorenz & Kopf, LLP

(57) ABSTRACT

The present disclosure relates to a sprayable gel composition for hair conditioning, comprising (a) from about 0.01% to about 0.35% by weight of an acrylate/alkyl-acrylate crosspolymer, (b) from about 0.1% to about 30% by weight of a silicone oil selected from dimethylpolysiloxane, cyclic polysiloxanes, hydroxyl-terminated polydimethylsiloxanes, polysiloxane-polyalkylene copolymers, alkyl methyl polysiloxanes, phenylmethylpolysiloxane, hydroxyl-terminated polydimethylsiloxanes, divinyldimethicone/dimethicone copolymer, and combination thereof, (c) from about 0.1% to about 30% by weight of a monohydric alcohol containing from about 2 to about 8 carbon atoms, and (d) from about 40% to about 99.9% by weight of a cosmetically acceptable carrier, and to a method of treating hair in need of a conditioning treatment

16 Claims, 2 Drawing Sheets

SPRAYABLE GEL COMPOSITION FOR HAIR CONDITIONING

CROSS-REFERENCE TO RELATED APPLICATION

This application is a U.S. National-Stage entry under 35 U.S.C. § 371 based on International Application No. PCT/CN2015/096803, filed Dec. 9, 2015 which was published under PCT Article 21(2).

TECHNICAL FIELD

The present disclosure relates to a sprayable gel composition for hair conditioning, and to a method of treating hair in need of a conditioning treatment.

BACKGROUND

Various types of hair conditioners have been widely used in hair dressing practice. Among them, gel-type of hair conditioners have become popular due to their attractive appearance which may attribute to gain more customers.

However, due to the viscous nature of hair conditioners in gel type, these conditioners are typically dispensed directly through the portal of the container and are pumped through a large orifice. Regardless of which type of dispensing system is used, a large quantity of the gel is dispensed into the hands of the beautician or user followed by vigorous rubbing of the hands, in order to liquefy the gel. If the gel conditioner is dispensed through smaller orifices, it may cause the orifices to clog and become unusable.

Prior art attempts to solve the problem can be found for example in U.S. Pat. No. 5,340,570 B and WO1994014404 A1 both of which disclose that by incorporating an alkyl polyol and a water soluble or emulsifiable silicone based compound into a moderately viscous gel-type hair conditioning composition, a hair conditioning gel formulation is attained which is able to be delivered in a spray mist pattern using conventional small diametered pump spray nozzles.

However, there is still a need to provide a sprayable gel composition for hair conditioning which is capable of being dispensed quickly and easily in a mist-type spray form through small diameter nozzles, and not only provides excellent spray characteristics but also delivers excellent sensory properties.

SUMMARY

Based on the foregoing discussion, an object of the present disclosure is to provide a sprayable gel composition for hair conditioning, comprising:
(a) from about 0.01% to about 0.35% by weight of an acrylate/alkyl-acrylate cross-polymer,
(b) from about 0.1% to about 30% by weight of a silicone oil selected from dimethylpolysiloxane, cyclic polysiloxanes, hydroxyl-terminated polydimethylsiloxanes, polysiloxane-polyalkylene copolymers, alkyl methyl polysiloxanes, phenylmethylpolysiloxane, hydroxyl-terminated polydimethylsiloxanes, divinyldimethicone/dimethicone copolymer, and combination thereof,
(c) from about 0.1% to about 30% by weight of a monohydric alcohol containing from about 2 to about 8 carbon atoms, and
(d) from about 40% to about 99.9% by weight of a cosmetically acceptable carrier, wherein the weight percentages are based on the total weight of all components of the sprayable gel composition for hair conditioning.

Also provided is a method of treating hair in need of a conditioning treatment, the method comprising the step of topically applying the sprayable gel composition for hair conditioning according to the present disclosure as a spray to the hair to be conditioned.

It was surprisingly found that the sprayable gel composition for hair conditioning allows to exert a remarkable performance of passing through small diameter nozzles, e.g. from about 0.5 mm to about 1 mm and spraying mist as well as an excellent hair conditioning profile.

These and other objects, features and advantages of the present disclosure will become better understood upon having reference to the following description of the disclosure.

DETAILED DESCRIPTION

Figure 1:
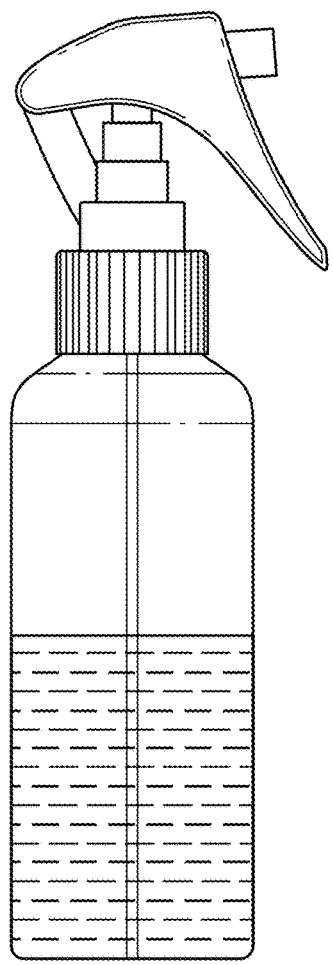
FIG. 1 is a picture of the sprayer used in the spraying test.

The following detailed description is merely exemplary in nature and is not intended to limit the disclosure or the application and uses of the subject matter as described herein. Furthermore, there is no intention to be bound by any theory presented in the preceding background or the following detailed description.

It is to be understood by one of ordinary skill in the art that the present application is a description of exemplary embodiments only, and is not intended as limiting the broader aspects of the present disclosure.

As used herein, "sprayable" means that the gel composition can be released in the form of dissipated particles. The dissipated particles can have varying shapes, consistencies, and sizes. The properties of the sprayed particles can include everything from fine aerosol atomized spray to liquid drops, snow-like drops, solid spray flakes and spray foam.

Herein, "mixture" is meant to include a simple combination of materials and any compounds that may result from their combination.

All percentages listed in this specification are percentages of components by weight, unless otherwise specifically mentioned.

The present disclosure is directed to sprayable gel composition for hair conditioning, comprising:
(a) from about 0.01% to about 0.35% by weight of an acrylate/alkyl-acrylate cross-polymer,
(b) from about 0.1% to about 30% by weight of a silicone oil selected from dimethylpolysiloxane, cyclic polysiloxanes, hydroxyl-terminated polydimethylsiloxanes, polysiloxane-polyalkylene copolymers, alkyl methyl polysiloxanes, phenylmethylpolysiloxane, hydroxyl-terminated polydimethylsiloxanes, divinyldimethicone/dimethicone copolymer, and combination thereof,
(c) from about 0.1% to about 30% by weight of a monohydric alcohol containing from about 2 to about 8 carbon atoms, and
(d) from about 40% to about 99.9% by weight of a cosmetically acceptable carrier, wherein the weight percentages are based on the total weight of all components of the sprayable gel composition for hair conditioning.

Acrylate/Alkyl-Acrylate Cross-Polymer

The acrylate/alkyl-acrylate cross-polymers suitable to be used in the present disclosure act as rheology modifier, which have benefits such as thickening with a wide range of flow properties, high suspension of insoluble components, broad temperature stability, etc. Acrylate/alkyl-acrylate cross-polymers have been widely used in styling gel, shampoo, conditioner, mousse, hair dyeing/coloring, permanent waves.

In one embodiment of the present disclosure, the acrylate/alkyl-acrylate cross-polymers are selected from (listed as INCI names) Acrylate/C10-30 Alkyl-acrylate Cross-polymer, Poly C10-30 Alkyl-acrylate, Potassium acrylate/C10-30 Alkyl-acrylate cross-polymer, Sodium acrylate/C10-30 Alkyl acrylate Cross-polymer. The official chemical description of each of these chemical names can be found in the INCI dictionary or at the website (www.ctfa.org).

The cross-polymer acrylate/alkyl-acrylate is present in an amount of from about 0.05% to about 0.35%, preferably from about 0.1% to about 0.3%, based on the total weight of all components of the sprayable gel composition for hair conditioning.

Preferably, the acrylate/alkyl acrylate cross-polymer is one or more of acrylate/C10-30 alkyl-acrylate cross-polymers, which are copolymers of C10-30 alkyl acrylate and one or more monomers of acrylic acid, methacrylic acid or one of their mono-esters crosslinked with an allyl (2-propenyl) ether of sucrose or an allyl ether of pentaerythritol.

Essentially, the Acrylate/C10-30 Alkyl-acrylate Cross-polymer acts like an emulsifying polymer of the formulation and is a component that is compatible with most of the cosmetic adjuvants usually employed in emulsion, such as oils and emollient esters and co-solvents, film-forming and wetting agents, preservatives, chelating agents and antioxidants, fragrances, colorings and even low HLB value surfactants.

Commercially, the acrylate/alkyl-acrylate cross-polymers are available from Lubrizol Corporation under the trade name Carbopol® as a series of products of polymeric rheology modifiers such as Carbopol® ETD 2020, Carbopol® Ultrez 20, and Carbopol® Ultrez 21.

Depending on the crosslinking density, the acrylate/alkyl acrylate cross-polymers used in the sprayable gel composition possess a suitable yield value. Yield value, also referred to as yield stress, is defined as the initial resistance to flow under stress. It is measured by the Brookfield Yield Value (BYV) Extrapolation Method using a Brookfield viscometer (Model RVT) at ambient room temperature of from about 20 to about 25° C. The yield value is an extrapolation of measured values to a shear rate of zero. The BYV in dyn/cm$^2$ is calculated by the following equation:

$$BYV=(\eta_{\alpha 1}-\eta_{\alpha 2})/100$$

where $\eta_{\alpha 1}$ and $\eta_{\alpha 2}$=apparent viscosities obtained at two different spindle speeds (0.5 rpm and 1.0 rpm, respectively). These techniques and the usefulness of the yield value measurement are explained in Technical Data Sheet Number 244 (Revision: May 1998) from Noveon Consumer Specialties of Lubrizol Advanced Materials, Inc., herein incorporated by reference.

In one embodiment of the present disclosure, the acrylate/alkyl-acrylate cross-polymer, preferably Acrylate/C10-30 Alkyl-acrylate Cross-polymer has a Brookfield yield value in the range of from about 500 to about 3000 dyn/cm$^2$, preferably from about 700 to about 2500 dyn/cm$^2$, more preferably from about 800 to about 2200 dyn/cm$^2$, as measured in a 0.2% by weight of aqueous solution.

Silicone Oil

The compositions of the present disclosure further contains a silicone oil. It is believed that the silicone oil can provide smoothness and softness on dry hair.

The silicone oil can be a fluid organopolysiloxane or a fluid organopolysiloxane composition, which for example have a bulk viscosity of at least about 1 or about 5 up to about 1000000 centiStokes or even up to about 20000000 centiStokes (about 1 or about 5 mm$^2$/sec up to about 1 or even about 20 m$^2$/sec.)

Suitable silicone oils according to the present disclosure are polyorganosiloxanes such as for example dimethylpolysiloxane [INCI dimethicone, e.g. Abil 10 to 10 000 (Goldschmidt) or Xiameter PMX 200 Silicone fluid (Dow Corning)]; cyclic polysiloxanes such as e.g. cyclopentasiloxane; octamethylcyclotetrasiloxane, hexamethyl cyclotrisiloxane and decamethylcyclopentasiloxane which are also designated according to INCI as Cyclomethicone and are e.g. commercially available as Dow Corning 245 Fluid, Dow Corning 244 Fluid or Xiameter PMX 0245; polysiloxane-polyalkylene copolymers (PEG Dimethicone, such as PEG-7 Dimethicone, PEG-12 Dimethicone, PEG/PPG Dimethicone such as PEG/PPG-12/18 Dimethicone, PEG/PPG-18/6 Dimethicone, PEG/PPG-18/18 Dimethicone, PEG/PPG-19/19 Dimethicone, PEG/PPG-27/27 Dimethicone); alkyl methyl polysiloxanes such as cetyl dimethicone (Dow Corning 2502 cosmetic Fluid, Abil® wax 9801), Trisiloxane, Octamethyltrisiloxane; functional silicone fluids such as phenylmethylpolysiloxane (INCI: Phenyl Dimethicone, phenyl trimethicone such as e.g. Dow corning 556 Cosmetic Grade Fluid); trimethyl pentaphenyl trisiloxane (Dow Corning PH 1555), hydroxyl-terminated polydimethylsiloxanes, such as Dimethiconol (Dow Corning 1501 Fluid and 1503 Fluid), silicone gum blends such as cyclopentasiloxane and dimethiconol (Dow Corning 1501 Fluid), dimethiconol (Dow Corning 1503 Fluid) and bis-hydroxyethoxypropyl dimethicone (Dow Corning 5562), and divinyldimethicone/dimethicone copolymer (Dow Corning 2220).

In one embodiment of the present disclosure, the silicone oil is selected from dimethylpolysiloxanes, cyclic polysiloxanes, hydroxyl-terminated polydimethylsiloxanes, polysiloxane-polyalkylene copolymers, alkyl methyl polysiloxanes, phenylmethylpolysiloxanes, hydroxyl-terminated polydimethylsiloxanes, divinyldimethicone/dimethicone copolymers, and combination thereof.

In one preferred embodiment, the silicone oil is selected from dimethylpolysiloxanes, cyclic polysiloxanes, polysiloxane-polyalkylene copolymers and phenylmethylpolysiloxanes, and combination thereof, and combination thereof.

The silicone oils herein present in an amount of from about 1% to about 10%, preferably from about 5% to about 9%, based on the total weight of all components of the sprayable gel composition for hair conditioning.

According to the present disclosure, it has been found that amino/amide modified organopolysiloxanes are not suitable to be used in the composition, and thus the composition according to the present disclosure essentially contains no amino/amide modified organopolysiloxanes.

In the present disclosure, "essentially contains no amino/amide modified organopolysiloxanes" means that the present composition contains no amino/amide modified organopolysiloxanes; the present composition contains no amino/amide modified organopolysiloxanes other than impurities of the ingredients; or, if the present composition contains amino/amide modified organopolysiloxanes, the level of such amino/amide modified organopolysiloxanes is very low. In the present disclosure, a total level of such amino/amide modified organopolysiloxanes in the present composition, if included, preferably about 1% or less, more preferably about 0.5% or less, still more preferably about 0.1% or less by weight of all components of the present composition.

Monohydric Alcohol

According to the present disclosure, the sprayable gel composition for hair conditioning further contains a monohydric alcohol containing from about 2 to about 8 carbon atoms.

For purpose of this disclosure, and as used in this specification and the appended claims, the term "monohydric alcohol" is defined as an alcohol having from about 2 to about 8 carbon atoms and one hydroxyl functional group, such as ethanol, butanol, methanol or isopropanol, preferably ethanol, which is present in an amount that is allowed to be used in cosmetic compositions according to the legislation and the international cosmetic regulations.

In one embodiment of the present disclosure, the monohydric alcohol is present in an amount of from about 1% to about 30%, preferably from about 1% to about 15%, more preferably from about 3% to about 5% by weight, based on the total weight of all components of the sprayable gel composition for hair conditioning.

It is believed that the monohydric alcohols act as co-solvent in the composition system so as to allow the solubilization of the water phase and oil phase and more specifically so as to compensate for the natural incompatibility manifested in terms of solubility between the silicone oil and the water-soluble materials. It has been found that other co-solvents such as polyols are not suitable to be used in the composition and exhibited poor spraying effect if included in the composition, and thus the composition according to the present disclosure essentially contains no polyols.

In the present disclosure, "essentially contains no polyols" means that the present composition contains no polyols such as diols, e.g. butylene glycol, propylene glycol, ethylene glycol, and glycerin; the present composition contains no polyols other than impurities of the ingredients; or, if the present composition contains polyols, the level of such polyols is very low. In the present disclosure, a total level of such polyols in the present composition, if included, preferably about 1% or less, more preferably about 0.5% or less, still more preferably about 0.1% or less by weight of all components of the present composition.

Cosmetically Acceptable Carrier

The compositions of the present disclosure also include at least one cosmetically acceptable carrier. A cosmetically acceptable carrier refers to any organic or aqueous solvent or solvent system that is compatible with the other components of the disclosure and suitable for human use. However, persons skilled in the art would appreciate that not every carrier for the polymer and metal is "cosmetically acceptable". Examples of non-cosmetically acceptable carriers include tetrahydrofuran, dimethyl sulfoxide, benezene, benezene derivatives, and dimethylformamide. In addition, carriers that are toxic, abrasive, or in any way damaging to keratinous substrates such as hair should not be utilized.

Generally, cosmetically acceptable carriers may be selected from volatile organic solvents, non-volatile organic solvents, water, and mixtures thereof. Alcohols that may be utilized as carriers include $C_1$ to $C_{20}$ straight chain, branched, or cyclic mono-alcohols, including ethanol, propanol, butanol, tert-butanol, isopropanol and mixtures thereof. Other cosmetically acceptable carriers such as hydrocarbons (e.g., mineral oils, mineral solvents, mineral spirits, petroleum, waxes, synthetic hydrocarbons, animal oils, vegetable oils, and volatile hydrocarbons (e.g., isododecane)), light paraffinic solvents, and non-hydrocarbon solvents (e.g., amyl acetate, butyl acetate, isobutyl acetate, ethyl acetate, propyl acetate and isopropyl acetate) may also be useful. Preferably, the cosmetically acceptable carrier is water, more preferably deionized water.

The cosmetically acceptable carrier is present in an amount of from about 40 to about 99.9% by weight, preferably from about 60 to about 99.5% by weight, and more preferably from about 80 to about 99% by weight based on the total weight of all components of the cosmetic composition.

Neutralizing Agent

The composition according to the present disclosure optionally contains a neutralizing agent present in a sufficient amount that results in the pH value of the composition being from about 5 to about 7.

The neutralizing agent of the present disclosure can be selected from alkaline metal and alkaline metal earth hydroxides, ammonia, primary, secondary amines, tertiary amines, alkanolamines hydroxyamines or any other neutralizing agent known on the market that acts in the same way as those already mentioned, as well as mixture thereof.

Suitable neutralizing agents which may be utilized in this manner include, but are not limited to, alkaline metal and alkaline metal earth hydroxides, such as sodium or potassium hydroxide, ammonia, primary, secondary and tertiary amines; alkanolamines; and, hydroxyamines, such as 2-amino-2-methyl-propanol, 2-amino-2-methyl-1,3-propanediol (AMP) and triethanol amine (TEA) and mixtures thereof.

Optional Components

In the cosmetic composition for skin brightening of the present disclosure, there may be added various cosmetic adjuvants selected from emollients, emulsifiers, vitamins, hormones, amino acids, surfactants, colorants, dyes, pigments, fragrances, odor absorbers, antiseptics, preservatives, bactericides, humectants, thickeners, solvents, fillers, antioxidants, sequestering agents, sunscreens, or any other known components and additives as long as the effects of the present disclosure are not impaired.

Examples of suitable emollients nonexclusively include mineral oil, lanolin, plant-derived oils including but not limited to cocoglycerides, coconut oil, palm kernel oil, babssu oil, sunflower seed oil, japan wax, palm oil, apricot kernel oil, tallow, argan oil, baobab oil, cocoa butter, andiroba seed oil, mango butter, avocado oil, cottonseed oil, rice bran oil, shea butter, marula oil, *papaya* seed oil, pumpkin seed oil, wheat germ oil, illipe butter, corn oil, olive oil, poppy seed oil, grapeseed oil, sesam oil, yangu seed oil, sweet almond oil, hazelnut oil, soybean oil, acai oil, safflower oil, hydbrid safflower oil, walnut oil, canola oil, black currant seed oil, hazel seed oil, peanut oil, cranberry seed oil, tall oil, kokum butter, manketti nut oil, moringa oil, raspberry seed oil, cupuacu butter, linseed oil, tung oil, jojoba oil, borage seed oil, evenining primrose oil, veronica oil, ongokea oil], vegetable oils, isostearyl isostearate, glyceryl laurate, methyl gluceth-10, methyl gluceth-20 chitosan, dicaprylylether, and mixtures thereof.

Emulsifiers and co-emulsifiers that may be used include, for example, carboxyvinyl polymers of high molecular weight (for example Carbopol®), polysorbates (for example Tween 20® or Tween 60), sorbitan esters and in particular a sorbitan monostearate, tristearate, monopalmitate or laurate. Other emulsifiers such as various stearic acid or palmitic acid derivatives, for example PEG-100 stearate, stearic acid or palmitic acid mono- or diglycerides, a self-emulsifying propylene glycol stearate, or polyglyceryl 2-sesquioleate, polyoxyethylene cetyl ether, a siloxane polyglucoside or an emulsifiable silicone may also be used.

Examples of UV screening agent nonexclusively include benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate 0, red petrolatum, and mixtures thereof.

Fragrance components and mixtures thereof may be obtained from natural products such as essential oils, absolutes, resinoids, resins and concretes, as well as synthetic products such as hydrocarbons, alcohols, aldehydes, ketones, ethers, carboxylic acids, esters, acetals, ketals, nitriles and the like, including saturated and unsaturated compounds, aliphatic, carbocyclic and heterocyclic compounds.

The surfactant may be selected from anionic, nonionic, cationic and amphoteric actives. Particularly preferred non-ionic surfactants are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from about 2 to about 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof.

Amounts of these cosmetic adjuvants may range from about 0.001% to about 20% by weight based on the total weight of all components of the cosmetic composition.

In one embodiment, the sprayable composition according to the present disclosure has a viscosity in the range of from about 100 to about 10000 mPa·s, preferably from about 100 to about 7000 mPa·s, and more preferably from about 3000 to about 5000 mPa·s.

The viscosity of the sprayable composition in the specification was measured by Brookfield rotating spindle method (all viscosity measurements reported herein are conducted by the Brookfield method whether mentioned or not). The viscosity measurements are calculated in mPa·s, employing a Brookfield rotating spindle viscometer, Model RVT (Brookfield Engineering Laboratories, Inc.), at about 20 rpm, at ambient room temperature of about 20 to about 25° C. Spindle sizes were selected in accordance with the standard operating recommendations from the manufacturer. Generally, spindle sizes were selected as follows:

| Spindle Size No. | Viscosity Range (mPa · s) |
|---|---|
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. A person skilled in the art will select a spindle size appropriate for the system to be measured.

In a preferred embodiment, the present disclosure discloses a sprayable gel composition for hair conditioning, comprising:

(a) from about 0.1% to about 0.3% by weight of acrylates/C10-30 alkyl acrylate crosspolymers, (b) from about 5% to about 9% by weight of silicone oil selected from dimethylpolysiloxane, cyclic polysiloxanes, polysiloxane-polyalkylene copolymers and phenylmethylpolysiloxane, (c) from about 3% to about 5% by weight of ethanol, (d) from about 0.01% to about 2% by weight of neutralizing agent, and (e) from about 85% to about 95% by weight of deionized water, wherein the weight percentages are based on the total weight of all components of the sprayable gel composition for hair conditioning.

In another aspect, the present disclosure also discloses a method of treating hair in need of a conditioning treatment, the method comprising the step of topically applying the sprayable gel composition for hair conditioning according to the present disclosure as a spray to the hair to be conditioned.

Surprisingly, the cosmetic composition according to the present disclosure exhibited an excellent spraying effect through small nozzles as well as an excellent conditioning performance.

The present disclosure may be better understood with reference to the following examples.

Examples

Materials:

Carbopol Ultrez 21 is the trade name of Acrylate/C10-30 Alkyl-acrylate Cross-polymer (INCI name) commercially available from Lubrizol and has a Broodfield yield value of about 2100 dyn/cm2 as measured in a 0.2% by weight of aqueous solution.

Carbopol ETD 2020 is the trade name of Acrylate/C10-30 Alkyl-acrylate Cross-polymer (INCI name) commercially available from Lubrizol and has a Broodfield yield value of about 1070 dyn/cm$^2$ as measured in a 0.2% by weight of aqueous solution Carbopol Ultrez 20 is the trade name of Acrylate/C10-30 Alkyl-acrylate Cross-polymer (INCI name) commercially available from Lubrizol and has a Broodfield yield value of about 870 dyn/cm$^2$ as measured in a 0.2% by weight of aqueous solution.

Tego 140 is the trade name of Carbomer (INCI name for polyvinyl carboxy polymer cross-linked with ethers of pentaerythritol) commercially available from Evonik.

Aculyn 38 is the trade name of Acrylates/Beheneth-26 Methacrylate Copolymer (INCI name) commercially available from Dow Chemical.

PMX 200 1cs is the trade name of a Trisiloxane (INCI name) commercially available from Dow Corning.

PMX 200 5cs is the trade name of a Dimethicone (INCI name) commercially available from Dow Corning.

PMX-0245 4cs is the trade name of a Cyclopentasiloxane (INCI name) commercially available from Dow Corning.

DC 1501 Fluid is the trade name of Cyclopentasiloxane mixed with Dimethiconol (INCI name) commercially available from Dow Corning.

DC 1503 Fluid is the trade name of Dimethicone mixed with Dimethiconol (INCI name) commercially available from Dow Corning.

DC 5225 C is the trade name of Cyclopentasiloxane mixed with PEG/PPG-18/18 Dimethicone (INCI name) commercially available from Dow Corning.

DC 1664 is the trade name of Dimethicone mixed with Laureth-4 and Laureth-23 (INCI name) commercially available from Dow Corning.

DC 2220 is the trade name of Divinyldimethicone/Dimethicone Copolymer mixed with C12-13 Pareth-23 and C12-13 Pareth-3 (INCI name) commercially available from Dow Corning.

DC 8170 is the trade name of Amodimethicone mixed with C11-15 Pareth-7, Laureth-9, Glycerin and Trideceth-12 (INCI name) commercially available from Dow Corning.

DC 949 is the trade name of Amodimethicone mixed with C11-15 Pareth-7, Laureth-9, Glycerin and Trideceth-12 (INCI name) commercially available from Dow Corning.

DC 8170 is the trade name of Amodimethicone mixed with Cetrimonium Chloride and Trideceth-12. (INCI name) commercially available from Dow Corning.

DC 8401 is the trade name of Bis-Isobutyl PEG/PPG-20/35/Amodimethicone Copolymer mixed with Cetyl Ethylhexanoate, Polysorbate 80 and Butylene Glycol (INCI name) commercially available from Dow Corning.

DC 556 22.5cs is the trade name of Phenyl Trimethicone (INCI name) commercially available from Dow Corning.

DC 1874 is the trade name of PEG-7 Dimethicone mixed with Laureth-7 and Polysorbate 20 (INCI name) commercially available from Dow Corning.

DC 0193 is the trade name of PEG-12 Dimethicone (INCI name) commercially available from Dow Corning.

Ethanol is commercially available from Sasol.

Glycerin is commercially available from Univar.

Butylene glycol is commercially available from Univar.

Propylene glycol is commercially available from BASF.

NaOH is commercially available from Merck.

Cetiol OE is dicaprylyl ether commercially available from BASF under the trade name Cetiol OE.

Benzophenone-4 is commercially available from BASF under the trade name Uvinul MS 40.

ProSina is the trade name of a hydrolysed keratin commercially available from Croda.

Croquat WKP-PE-LQ-(WD) is the trade name of Cocodimonium Hydroxypropyl Hydrolyzed Keratin (INCI name) commercially available from Croda.

Nutrilan Keratin W PP is the trade name of a protein hydrolysate commercially available from BASF.

D-Panthenol 75% is an aqueous solution of pure Panthenol, stabilized with 0.3% citric acid commercially available from BASF.

Parfum 414881 Deep White is fragrance commercially available from Firmenich GmbH.

Yellow No. 6 is pigment CI 15985 ($C_{16}H_{10}N_2Na_2O_7S_2$) commercially available from BASF.

Red 4R is pigment CI 16255 ($C_{20}H_{11}N_2Na_3O_{10}S_3$) commercially available from Sigma-Aldrich.

PEG-40 Hydrogenated Caster Oil is commercially available from BASF.

Phenonip ME is the trade name of Phenoxyethanol mixed with Methylparaben and Ethylparaben (INCI name) commercially available from Clariant.

Examples in accordance with the present disclosure and comparative examples

Example 1 was prepared according to the formulation as shown in Table 1.

TABLE 1

| Material | Amount (g) |
| --- | --- |
| Carbopol Ultrez 21 | 0.3 |
| Ethanol | 5.0 |
| DC 556 | 1.0 |
| PMX 200 1 cs | 5.0 |
| DC 5225 C | 3.0 |
| NaOH | 0.07 |
| Cetiol OE | 2.00 |
| Benzophenone-4 | 0.05 |
| ProSina | 0.01 |
| Croquat WKP-PE-LQ-(WD) | 0.01 |
| Nutrilan Keratin W PP | 0.04 |
| D-Panthenol 75% | 0.20 |
| Parfum 414881 Deep White | 0.20 |
| Yellow No. 6 | 0.00015 |
| Red 4R | 0.00017 |
| PEG-40 Hydrogenated Caster Oil | 0.50 |
| Phenonip ME | 0.40 |
| Deionized water | Up to 100 |

The materials were divided into the following groups:
Group 1: Carbopol Ultrez 21 and deionized water;
Group 2: ethanol, DC 556, PMX 200 1cs and DC 5225 C;
Group 3: Cetiol OE;
Group 4: Parfum 414881 Deep White, PEG-40 Hydrogenated Caster Oil, Phenonip ME;
Group 5: NaOH;
Group 6: Benzophenone-4, ProSina, Croquat WKP-PE-LQ-(WD), Nutrilan Keratin W PP, D-Panthenol 75%, Yellow No. 6 and Red 4R.

The polymer (Carbopol Ultrez 21) of Group 1 was dispersed into deionized water until fully swelled at room temperature. The silicone oils in Group 2 was premixed with ethanol. Then the premix of Group 2 was slowly added into the mixture of Group 1 with proper agitation (stirring speed: 100 to 300 rpm) and fully dispersed until homogeneity. The material in Group 3 was added into the mixture as emollient. The materials in Group 4 was premixed and then added into the mixture. The material of Group 5 (neutralizer) was further added into the mixture with gentle agitation (stirring speed: 100 to 200 rpm), until the mixture was homogenous and thickened. Afterwards, the materials of Group 6 was added into the mixture to obtain a gel composition which has a viscosity of 3740 mPa·s and a pH value of 5.1.

The compositions of Examples 2 to 12 are the same as that of Example 1, except for the silicone oil replaced by 5% by weight of: PMX 200 1cs only, PMX 200 5cs, PMX-0245 4cs, DC 1501 Fluid, DC 1503 Fluid, DC 5225 C, DC 1664, DC 2220, DC 556 22.5cs, DC 1874, DC 0193, respectively, and balanced water. Examples 2 to 12 were prepared in the same manner as in Example 1.

The compositions of Comparative Examples 1 to 4 (CE 1 to 4) are the same as that of Example 1, except for the silicone oil replaced by 5% by weight of: DC 8566, DC 949, DC 8170, and DC 8401, respectively, and balanced water. Comparative Examples 1 to 4 were prepared in the same manner as in Example 1.

Example 13 was prepared according to the formulation as shown in Table 2.

TABLE 2

| Material | Amount (g) |
| --- | --- |
| Carbopol Ultrez 21 | 0.3 |
| Ethanol | 5.0 |
| DC 0193 | 5.0 |
| NaOH | 0.07 |

TABLE 2-continued

| Material | Amount (g) |
| --- | --- |
| Benzophenone-4 | 0.05 |
| Phenonip ME | 0.40 |
| Deionized water | Up to 100 |

The materials were divided into the following groups:
Group 1: Carbopol Ultrez 21 and deionized water;
Group 2: ethanol, DC 0193 and Phenonip ME;
Group 3: NaOH;
Group 4: Benzophenone-4.

The polymer (Carbopol Ultrez 21) of Group 1 was dispersed into deionized water until fully swelled at room temperature. The silicone oils in Group 2 was premixed with ethanol. Then the premix of Group 2 was slowly added into the mixture of Group 1 with proper agitation (stirring speed: 100 to 300 rpm) and fully dispersed until homogeneity. The material of Group 3 (neutralizer) was further added into the mixture with gentle agitation (stirring speed: 100 to 200 rpm), until the mixture was homogenous and thickened. Afterwards, the material of Group 4 was added into the mixture to obtain a gel composition.

The compositions of Comparative Examples 5 to 7 are the same as that of Example 13, except for the ethanol replaced by 5% by weight of glycerin, butylene glycol, propylene glycol, respectively, and balanced water. Comparative Examples 5 to 7 were prepared in the same manner as in Example 13.

Example 14 was prepared according to the formulation as shown in Table 3.

TABLE 3

| Material | Amount (g) |
| --- | --- |
| Carbopol Ultrez 21 | 0.2 |
| Ethanol | 5.0 |
| DC 556 | 1.0 |
| PMX 200 1 cs | 5.0 |
| DC 5225 C | 3.0 |
| NaOH | 0.07 |
| Cetiol OE | 2.00 |
| Benzophenone-4 | 0.05 |
| Parfum 414881 Deep White | 0.20 |
| PEG-40 Hydrogenated Caster Oil | 0.50 |
| Phenonip ME | 0.40 |
| Deionized water | Up to 100 |

The materials were divided into 6 groups:
Group 1: Carbopol Ultrez 21 and deionized water;
Group 2: ethanol, DC 556, PMX 200 1cs and DC 5225 C;
Group 3: Cetiol OE;
Group 4: Parfum 414881 Deep White, PEG-40 Hydrogenated Caster Oil, Phenonip ME;
Group 5: NaOH;
Group 6: Benzophenone-4.

The polymer (Carbopol Ultrez 21) of Group 1 was dispersed into deionized water until fully swelled at room temperature. The silicone oils in Group 2 was premixed with ethanol. Then the premix of Group 2 was slowly added into the mixture of Group 1 with proper agitation (stirring speed: 100 to 300 rpm) and fully dispersed until homogeneity. The material in Group 3 was added into the mixture as emollient. The materials in Group 4 was premixed and then added into the mixture. The material of Group 5 (neutralizer) was further added into the mixture with gentle agitation (stirring speed: 100 to 200 rpm), until the mixture was homogenous and thickened. Afterwards, the material of Group 6 was added into the mixture to obtain a gel composition which has a viscosity of 3050 mPa·s.

The compositions of Examples 15 to 16 are the same as that of Example 14, except for the rheology modifier replaced by 0.3% by weight of Carbopol Ultrez 21, 0.2% by weight of Carbopol Ultrez 20, respectively, and balanced water. Examples 15 to 16 were prepared in the same manner as in Example 14. The viscosity of compositions of Examples 15 to 16 is 4500 and 4210 mPa·s respectively.

The compositions of Comparative Examples 8 to 10 are the same as that of Example 14, except for the rheology modifier replaced by 0.5% by weight of Carbopol Ultrez 21, 0.2% by weight of Tego 140, 5% by weight of Aculyn 38, respectively, and balanced water. Examples 8 to 10 were prepared in the same manner as in Example 14.

Example 15 was prepared according to the formulation as shown in Table 4.

TABLE 4

| Material | Amount (g) |
| --- | --- |
| Carbopol Ultrez 21 | 0.3 |
| Ethanol | 5.0 |
| DC 556 | 1.0 |
| PMX 200 1 cs | 5.0 |
| DC 5225 C | 3.0 |
| Triethanolamine | 1.0 |
| Cetiol OE | 2.0 |
| ProSina | 0.01 |
| Parfum Velvet Hair | 0.30 |
| PEG-40 Hydrogenated Caster Oil | 0.60 |
| Deionized water | Up to 100 |

The materials were divided into the following groups:
Group 1: Carbopol Ultrez 21 and deionized water;
Group 2: ethanol, DC 556, PMX 200 1cs and DC 5225 C;
Group 3: Cetiol OE;
Group 4: Parfum Velvet Hair and PEG-40 Hydrogenated Caster Oil;
Group 5: Triethanolamine;
Group 6: ProSina.

The polymer (Carbopol Ultrez 21) of Group 1 was dispersed into deionized water until fully swelled at room temperature. The silicone oils in Group 2 was premixed with ethanol. Then the premix of Group 2 was slowly added into the mixture of Group 1 with proper agitation (stirring speed: 100 to 300 rpm) and fully dispersed until homogeneity. The material in Group 3 was added into the mixture as emollient. The materials in Group 4 was premixed and then added into the mixture. The material of Group 5 (neutralizer) was further added into the mixture with gentle agitation (stirring speed: 100 to 200 rpm), until the mixture was homogenous and thickened. Afterwards, the material of Group 6 was added into the mixture to obtain a gel composition.

Evaluation:

1. Miscibility Test

The following process was applied to determine the miscibility of the prepared products:

The preparation stability of the gel composition as-prepared was visually observed whether it was homogenous or flocs, particles, or other precipitates occurred immediately after the preparation. Furthermore, the storage stability of the gel composition stored under 45° C. and −15° C. for 1 month, respectively was visually observed whether the composition was still homogenous or phase separation occurred.

The test results are shown in Table 5.

TABLE 5

| Examples | Results | |
|---|---|---|
| | Preparation stability | Storage stability |
| Example 1 | Good | Good |
| Example 2 | Good | Good |
| Example 3 | Good | Good |
| Example 4 | Good | Good |
| Example 5 | Good | Good |
| Example 6 | Good | Good |
| Example 7 | Good | Good |
| Example 8 | Good | Good |
| Example 9 | Good | Good |
| Example 10 | Good | Good |
| Example 11 | Good | Good |
| Example 12 | Good | Good |
| Comparative Example 1 | White precipitates | N/A |
| Comparative Example 2 | Good | Phase separation |
| Comparative Example 3 | Good | Phase separation |
| Comparative Example 4 | White precipitates | N/A |

As is evident from the results of Table 5, the compositions containing selected types of silicone oils according to the present disclosure exhibited much better stability immediately after preparation and storage under extreme conditions than those containing amino/amide modified silicones.

2. Spraying Tests

Figure 2:
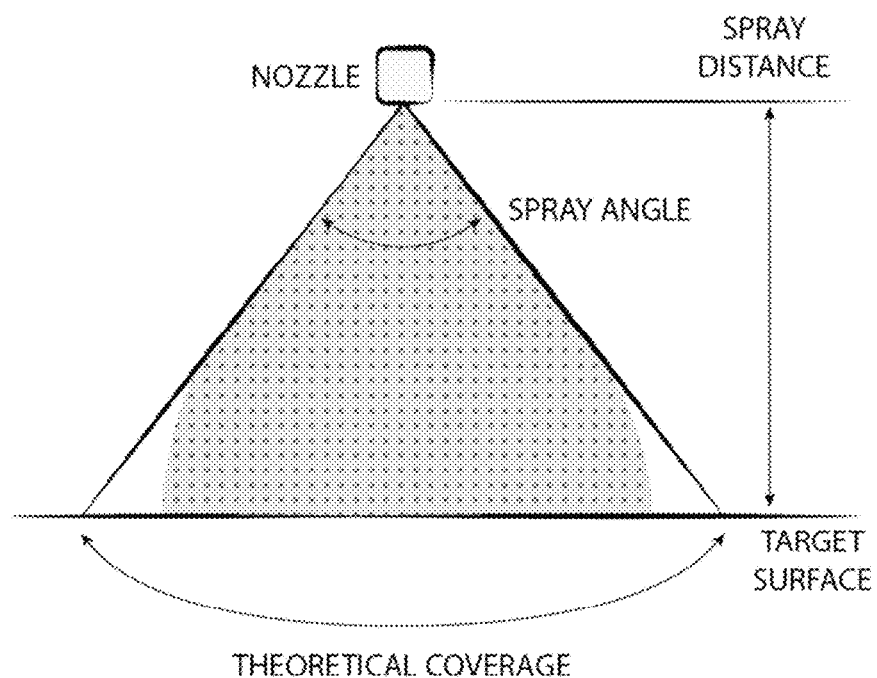
FIG. 2 is a scheme of the spraying area for the spraying test.

The following process was applied to determine the spraying effect of the prepared gel compositions:

The sprayer used in the test is shown in FIG. 1, and is commercially available from Model LM105, Ningbo Z&Z Sprayer Co., Ltd. The sprayer has a trigger lever, which activates a small pump. This pump is attached to a plastic tube that draws the gel composition from the bottom of the reservoir. The pump forces this liquid down a narrow barrel and out a small hole at the header. The hole or nozzle designed in full-cone type as illustrated in FIG. 2, serves to focus the flowing liquid so that it forms a concentrated stream. The nozzle is in the form of three-layer crater, and has a diameter of 0.8 mm and the spraying rate is 0.95±0.05 ml/s.

Figure 3:
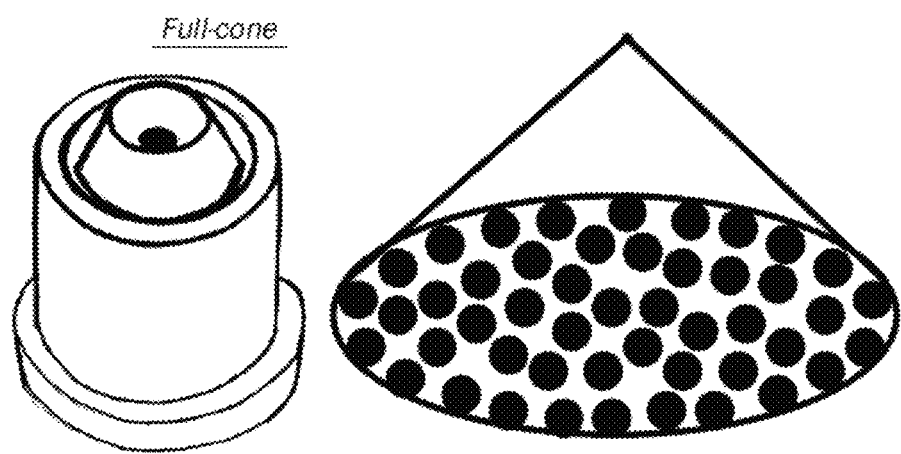
FIG. 3 is a scheme of the full-cone type nozzle equipped on the sprayer used in the spraying test and its spraying effect.

As shown in FIG. 3, a paper board with 1 cm×1 cm grids was placed in a manner that the surface of the paper board was parallel to the vertical axis of sprayer. The height of the nozzle was set to 15 cm, and the spraying distance between the outlet of the nozzle and target surface of paper board was set to 10 cm. The test was undergone by a practitioner in the art in 5 times for each example. The overall spraying area on the paper board was depicted and theoretical coverage of the ellipse spray pattern produced by the sprayer was calculated by the following formula:

$$S = \pi * a * b$$

in which S=Spraying area in cm$^2$; a=minor axis of the ellipse pattern in cm; and b=major axis of the ellipse pattern in cm.

The test results are shown in Tables 6 and 7.

TABLE 6

| Examples | Spraying area (cm$^2$) |
|---|---|
| Example 13 | 9.7 |
| Comparative Example 5 | 7.4 |
| Comparative Example 6 | 2.3 |
| Comparative Example 7 | 5.4 |

As can be seen from Table 6, the sprayable gel compositions containing ethanol (Example 13) produced a mist having a larger spraying area from a small nozzle than those containing polyols. It is believed that the much smaller spraying area was caused by the slight build-up of the deposits inside of the nozzle. Therefore, it is clear that the sprayable gel compositions containing ethanol according to the present disclosure possessed significantly better spraying performance than those containing polyols.

TABLE 7

| Examples | Spraying area (cm$^2$) |
|---|---|
| Example 14 | 54.4 |
| Example 15 | 20.2 |
| Example 16 | 14.76 |
| Comparative Example 8 | 0.85 |
| Comparative Example 9 | 7.3 |
| Comparative Example 10 | 9.3 |

It is demonstrated by the result of Table 7 that the spraying compositions for hair conditioning containing excess amount (0.5% by weight) of acrylate/alkyl-acrylate cross-polymers (Carbopol Ultrez 21) almost clogged the nozzle and exhibited much smaller spraying area than those containing suitable amount (0.2 and 0.3% by weight) of Carbopol Ultrez 21. In addition, The compositions containing acrylate/alkyl-acrylate cross-polymers (Carbopol Ultrez 20 and 21) in a suitable amount shown much better spraying effect than those containing other rheology modifiers commonly used in the art (Carbomer and Acrylates/Beheneth-26 Methacrylate Copolymer).

3. Conditioning Effect

The testing method for the conditioning profiles of the sprayable hair conditioning composition according to the present disclosure versus benchmark product (Extra Care Ultimate Repair Bi-Phase Serum commercially available from from Schwarzkopf & Henkel) was performed by the following steps:

1: Choose subjects having Asian hairs with normal or high level of damage to be subjected to the tests;

2: Wet the hair with warm water, and then apply 6 to 8 g shampoo (depending on the hair length of the subject) on the wet hair to lather and foam, and then rinse the hair copiously with warm water;

3: Apply 12 to 14 g of the hair conditioning composition to be tested (depending on the hair length of the subject) on the shampooed hair from the middle of hair to the ends of hair, spread the hair conditioning composition on the hair evenly, and rinse the conditioned hair copiously with warm water;

4: Dry the wet hair with a towel; and

5: Dry the hair completely with a hairdryer.

A panel of 4 professional hairdressers evaluated the properties of the hair conditioning compositions, including for example consistency, distribution on hair when applying, and the performance of hair, including smoothness, softness, combability in wet and dry conditions and appearance such as shine, heaviness, etc. The performances of each are sorted by level 0 to 6 as below, which was averaged by the total scores of the panel. The higher the number is, the better the performance is. If any performance of a composition is lower than 4, the composition is considered as not fulfilling the satisfaction of a person skilled in the art.

6: Very good,
5: Good,
4: Slightly good,
3: Slightly bad,
2: Bad, and
1: Very bad.

The results of the evaluation were listed in Table 8.

TABLE 8

| Test items | Example 15 | Benchmark |
|---|---|---|
| Combability of towel dried hair | 4.33 | 4.33 |
| Softness of towel dried hair | 4.33 | 4.33 |
| Drying time | 4.5 | 4.5 |
| Finger through when drying | 4.25 | 4.25 |
| Combability of blowing dried hair | 4.25 | 4.25 |
| Lightness of dried hair | 4.25 | 4.25 |
| Non overburdening | 4.75 | 4.75 |

As demonstrated in Table 8, the sprayable gel composition for hair conditioning possessed a good hair conditioning profile comparable to that of benchmark product.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A sprayable gel composition for hair conditioning, comprising:
    (a) from 0.1% to 0.3% by weight of an acrylate/alkyl-acrylate cross-polymer,
    (b) from about 1% to about 10% by weight of a silicone oil selected from dimethylpolysiloxanes, cyclic polysiloxanes, hydroxyl-terminated polydimethylsiloxanes, polysiloxane-polyalkylene copolymers, alkyl methyl polysiloxanes, phenylmethylpolysiloxanes, hydroxyl-terminated polydimethylsiloxanes, divinyldimethicone/dimethicone copolymers, and combinations thereof,
    (c) from about 1% to about 15% by weight of a monohydric alcohol containing from about 2 to about 8 carbon atoms, and
    (d) from about 40% to about 99.9% by weight of a cosmetically acceptable carrier,
    wherein the weight percentages are based on the total weight of all components of the sprayable gel composition for hair conditioning, and wherein the sprayable gel composition for hair conditioning is free of polyols.

2. The sprayable gel composition for hair conditioning according to claim 1, wherein the acrylate/alkyl acrylate cross-polymer is selected from:
    Acrylate/C10-30 Alkyl-acrylate Cross-polymer, Poly C10-30 Alkyl-acrylate, Potassium Acrylates/C10-30 Alkyl Acrylate Cross-polymer, Sodium Acrylates/C10-30 Alkyl Acrylate Cross-polymer, and mixtures thereof.

3. The sprayable gel composition for hair conditioning according to claim 1, wherein the acrylate/alkyl acrylate cross-polymer is one or more Acrylate/C10-30 Alkyl-acrylate Cross-polymers.

4. The sprayable gel composition for hair conditioning according to claim 1, wherein the silicone oil is selected from dimethylpolysiloxanes, polysiloxane-polyalkylene copolymers and phenylmethylpolysiloxanes, and combinations thereof.

5. The sprayable gel composition for hair conditioning according to claim 1, wherein the monohydric alcohol is selected from ethanol, butanol, methanol, isopropanol, or combinations thereof.

6. The sprayable gel composition for hair conditioning according to claim 1, wherein the sprayable gel composition for hair conditioning further comprises a neutralizing agent.

7. The sprayable gel composition for hair conditioning according to claim 1, wherein the neutralizing agent is selected from alkaline metal and alkaline metal earth hydroxides, ammonia, primary amines, secondary amines, tertiary amines, alkanolamines, hydroxyamines, and mixtures thereof.

8. The sprayable gel composition for hair conditioning according to claim 1, wherein the neutralizing agent is present in a sufficient amount to result in the pH value of the composition being from about 5 to about 7.

9. The sprayable gel composition for hair conditioning according to claim 1, wherein the sprayable gel composition for hair conditioning further comprise an additive selected from emollients, UV absorbing agents, moisturizers, active ingredients, colorants, surfactants, preservatives, emulsifiers, stabilizers and mixture thereof.

10. A sprayable gel composition for hair conditioning, comprising:
    (a) from 0.1% to 0.3% by weight of acrylates/C10-30 alkyl acrylate-crosspolymer,
    (b) from about 5% to about 9% by weight of silicone oil selected from dimethylpolysiloxane, cyclic polysiloxanes, -polysiloxane-polyalkylene copolymers, phenylmethylpolysiloxane, and combinations thereof,
    (c) from about 3% to about 5% by weight of ethanol,
    (d) from about 0.01% to about 2% of by weight of neutralizing agent, and
    (e) from about 80% to about 99% by weight of water,
    wherein the weight percentages are based on the total weight of all components of the sprayable gel composition for hair conditioning, and wherein the sprayable gel composition for hair conditioning is free of polyols.

11. A method of treating hair in need of a conditioning treatment, the method comprising the step of topically applying a sprayable gel composition for hair conditioning as a spray to the hair to be conditioned, wherein the sprayable gel composition comprises:
    (a) from 0.1% to 0.3% by weight of an acrylate/alkyl-acrylate cross-polymer,
    (b) from about 1% to about 10% by weight of a silicone oil selected from dimethylpolysiloxanes, cyclic polysiloxanes, hydroxyl-terminated polydimethylsiloxanes, polysiloxane-polyalkylene copolymers, alkyl methyl polysiloxanes, phenylmethylpolysiloxanes, hydroxyl-terminated polydimethylsiloxanes, divinyldimethicone/dimethicone copolymers, and combinations thereof, (c) from about 1% to about 15% by weight of a monohydric alcohol containing from about 2 to about 8 carbon atoms, and (d) from about 40% to about 99.9% by weight of a cosmetically acceptable carrier, wherein the weight percentages are based on the total weight of all components of the sprayable gel composition for hair conditioning, and wherein the sprayable gel composition for hair conditioning is free of polyols.

12. The sprayable gel composition for hair conditioning according to claim 1, wherein the silicone oil is present in an amount of from about 5% to about 9%, based on the total weight of all components of the sprayable gel composition for hair conditioning.

13. The sprayable gel composition for hair conditioning according to claim 1, wherein the monohydric alcohol is ethanol.

14. The sprayable gel composition for hair conditioning according to claim 1, wherein the monohydric alcohol is present in an amount of from about 3% to about 5% by weight, based on the total weight of all components of the sprayable gel composition for hair conditioning.

15. The sprayable gel composition for hair conditioning according to claim 1, wherein the acrylate/alkyl acrylate cross-polymer is one or more Acrylate/C10-30 Alkyl-acrylate Cross-polymers.

16. The sprayable gel composition for hair conditioning according to claim 15, wherein the silicone oil is present in an amount of from about 5% to about 9% by weight, based on the total weight of all components of the sprayable gel composition, and wherein the silicone oil is selected from dimethylpolysiloxane, polysiloxane-polyalkylene copolymers and phenylmethylpolysiloxane, and combinations thereof.

* * * * *